United States Patent
De La Torre

[11] Patent Number: 5,554,189
[45] Date of Patent: Sep. 10, 1996

[54] URETERAL PROSTHESIS

[76] Inventor: Fernando I. De La Torre, Rocafort 252 3° 2ª, 08029 Barcelona, Spain

[21] Appl. No.: 394,848

[22] Filed: Feb. 27, 1995

[30] Foreign Application Priority Data

Feb. 25, 1994 [ES] Spain ..................... 9400384

[51] Int. Cl.⁶ ..................................... A61F 2/02
[52] U.S. Cl. ............................. 623/11; 600/30
[58] Field of Search ................... 623/1, 11, 12; 600/36, 29, 30, 31; 606/191–200, 153, 158

[56] References Cited

U.S. PATENT DOCUMENTS

| | | | |
|---|---|---|---|
| 4,300,244 | 11/1981 | Bokros | 623/1 |
| 4,950,258 | 8/1990 | Kawai et al. | 604/281 |
| 5,108,407 | 4/1992 | Geremia et al. | 606/108 |
| 5,147,370 | 9/1992 | McNamara et al. | 606/108 |

Primary Examiner—Debra S. Brittingham
Attorney, Agent, or Firm—Michael J. Striker

[57] ABSTRACT

The lasting withdrawable ureteral prosthesis has a hollow tubular frame formed by a coiled biotolerable metallic wire including a number of closely contacting spires, at least a portion of which permit an easy flow of urine from an inside region to an outside region and from the outside region to the inside region of the hollow tubular frame, and a thin internal metallic wire, which is fastened, preferably by welding, to the three or four last spires at both ends of the tubular frame to prevent elastic elongation of the prosthesis. The internal metallic wire has hook-shaped internal wire ends in an undeformed configuration, and, after it is deformed from its undeformed configuration, returns immediately to the undeformed configuration to form the J-shaped curved ends of the hollow tubular frame one of which can occupy the pelvis of the kidney and the other, the urinary bladder of the patient. Furthermore an auxiliary metallic rod, which is much longer than the urethral prosthesis and which has a soft noninjurious end portion, can be inserted in the interior of the tubular frame of the ureteral prosthesis to keep the prosthesis straight during introduction into the patient.

5 Claims, 3 Drawing Sheets

FIG. 1
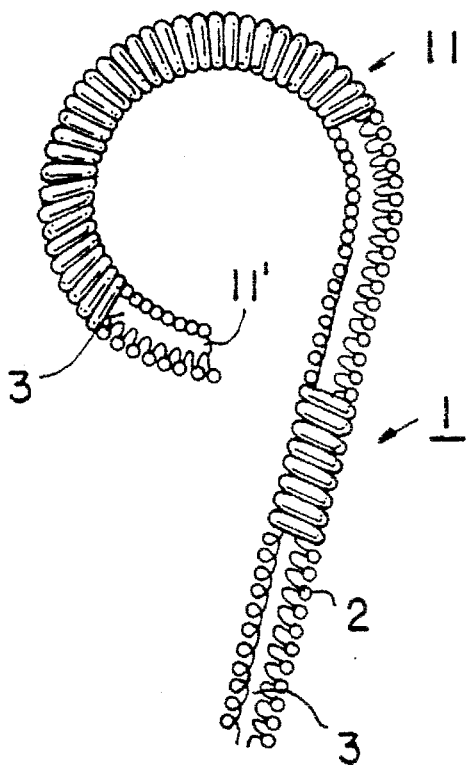
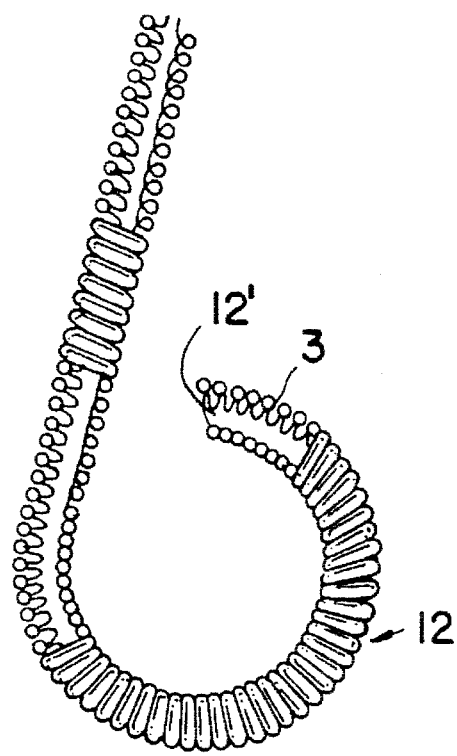
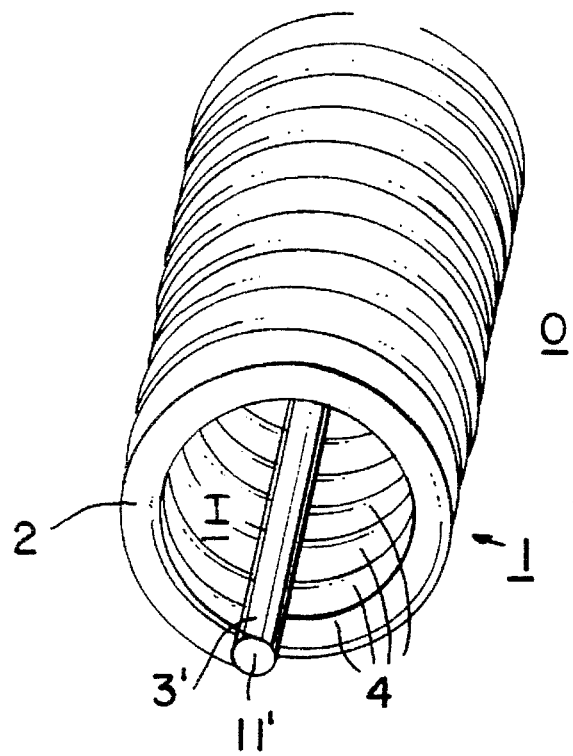
FIG. 2

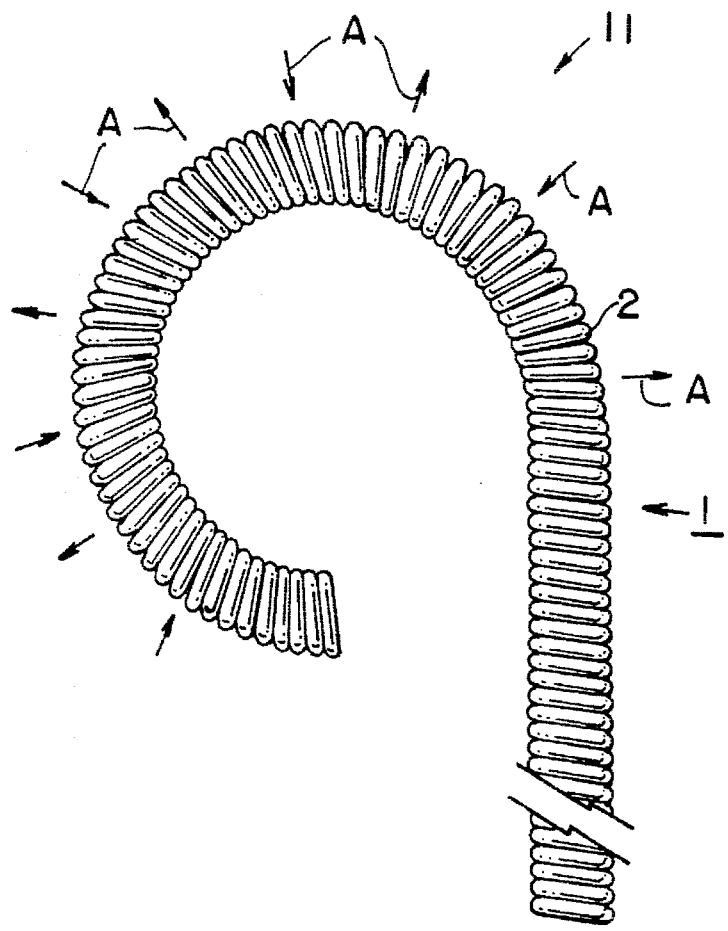
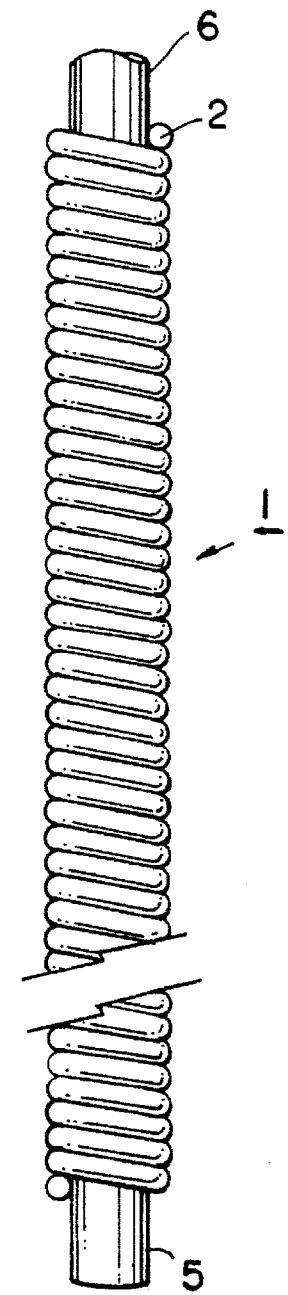
FIG.3
FIG.4

FIG. 5
FIG. 6
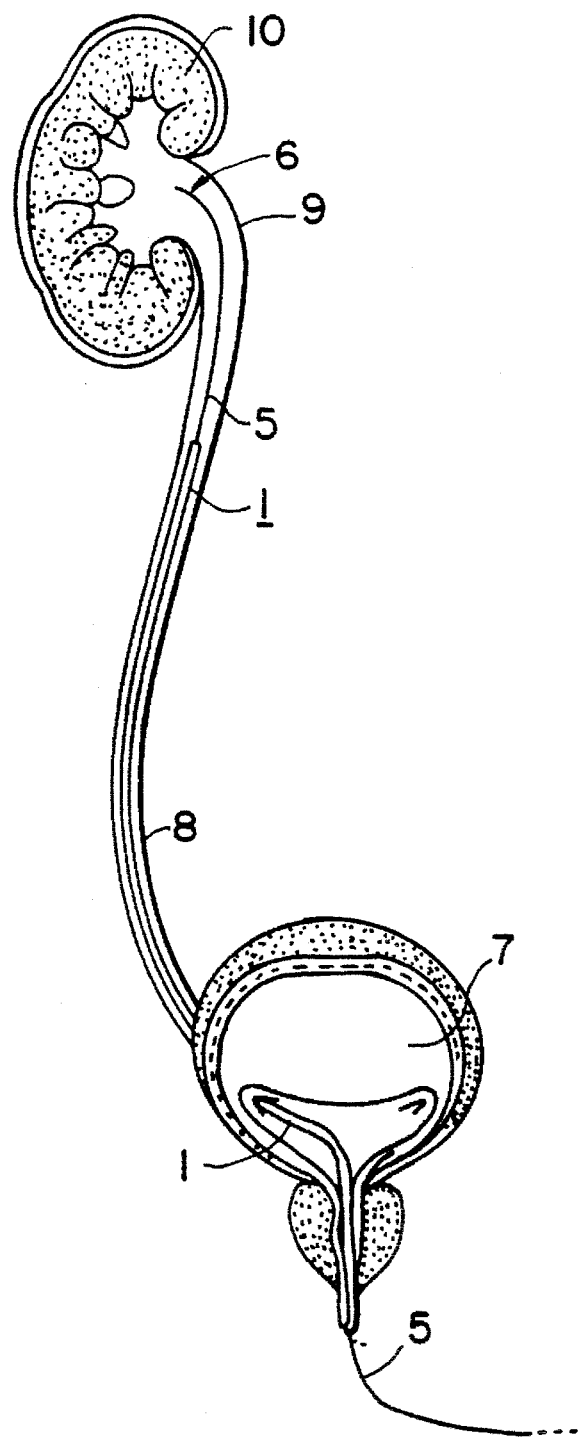
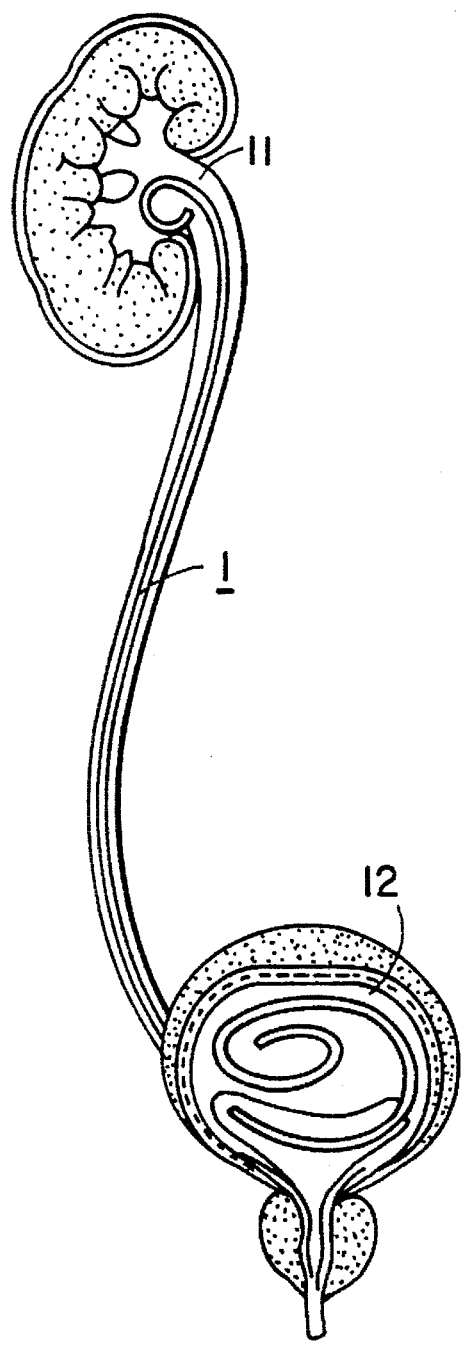

URETERAL PROSTHESIS

The present invention relates to an ureteral prosthesis of the withdrawable type, the essential characteristics of which allow its simple implantation and long life. Furthermore it may remain in the interior of the organism for periods of time greater than one year, allowing, as stated, its easy withdrawal, as well as its replacement by another one having the same characteristics.

The complementary endourologic techniques normally and presently very frequently used, as well as the supporting procedures prior to treatment, as well as the procedures required to overcome the complications which can arise, very often make necessary the use of an ureteral prosthesis, which must be placed in the interior of the organism.

The object of this prosthesis is to achieve the normal flow of urine from the kidney to the urinary bladder in those situations in which obstructive pathologic processes prevent it. It is likewise an object of this prosthesis to facilitate the disposal and elimination of calculus formed in the kidney. Either the calculus is expelled according to known methods, without breaking the calculus, or it is broken first by means of some of the presently available modern techniques. The placing of the prosthesis, in both cases, allows an easy and less painful disposal.

The permeability of the walls of the implanted prosthesis must at any moment allow and maintain the normal peristaltic dynamics of the urinary passage.

The ureteral prosthesis according to this invention is designed to be placed in the interior of the urinary passage, in such a way that it extends from the pelvis of the kidney to the urinary bladder through the ureter duct.

The placing as stated above within the urinary passage is generally achieved by anterograde or retrograde percutaneous methods or endoscopic procedures.

It is essential that the prosthesis be designed and produced in such a way that it may remain during a long time in the interior of the organism without losing its intrinsic properties, periods of time that, for patient comfort and the treatment effectiveness, conveniently extend even over one year.

The characteristics of the prosthesis must allow its easy withdrawal by endoscopic methods, allowing thus its quick replacement by another one having equal characteristics.

Certain basic characteristics of this type of ureteral prosthesis have been detailed which are sufficiently applied to the prosthesis of this invention.

So then specifically the main characteristics of this type of prosthesis according to the invention are summarized as follows:

The prosthesis must be easily inserted by any technical modality or means, as stated above, for example by endoscopic procedures, anterograde or retrograde percutaneous methods.

It must remain completely located in the interior, which is achieved in the arrangement of the prosthesis according to the invention, which occupies the whole ureter, from the pelvis of the kidney to the urinary bladder of the patient.

It must be designed so that any possibility of spontaneous displacement is prevented, which is guaranteed by an undeformed configuration having preformed ends in the shape of a hook or approximately J-shaped and a memory to recover this undeformed configuration after deformation. To achieve this an internal metallic wire is provided in the interior region of the ureteral prosthesis, which is fastened to both ends of the prosthesis so that any possibility of elastic elongation, which could be provoked by opposed pulling motions, is avoided.

This embodiment of the prosthesis must be easily withdrawable or replaceable, a characteristic which it must also possess, because these operations can be carried out by simply endoscopic methods.

The materials used to produce it must be radiopaque to allow its observation by X-ray apparatus and biologically inert or biotolerable and chemically stable, which is essential since it must remain in the interior of the organism without provoking rejection and without being attacked by liquids coming from the kidney.

The making of the prosthesis of the present invention in stainless steel wire of a suitable alloy allows the requirements of a satisfactory quality prosthesis to be fully met. These materials likewise prevent sediment incrustation.

A satisfactory urinary flow is guaranteed by the basic structure of the prosthesis, because the wire winding to form the wall of the prosthesis provides a great permeability, the normal peristaltic dynamics of the urinary passage being maintained in this way.

The material used confers on the prosthesis unit a good memory of its shape and undeformed configuration, namely with hook-shaped ends, while it provides a reasonable production cost, with an excellent cost-quality ratio, considering the medical use of this product.

The diseases which can be treated using the double-hook-shaped prosthesis, i.e., hook-shaped at each end, include chiefly the obstructions associated with inflammation of the ureter, obstructive anuria, acute obstruction, nephritic colic refractory to the chemiolithic treatment, obstructive lithiasis in pregnant women and iatrogenia in endoscopic surgery.

Considering the known prosthesis used up to now, it is convenient to emphasize the complications that can arise with an installed double-hook-shaped prosthesis and the characteristics of it which are not completely correct: urinary-sepsis infections, obstruction, incrustations, abnormal position, perforation and breakage, erosion, intense haematuria, spontaneous knot, this latter inconvenience being infrequent.

The following is a quick summary of the history of the prior art referring to these types of prosthesis. It should be mentioned an ureteral prosthesis was first used in the ureter early this century by Albarran. However, during the last few years new prosthesis models have been developed with tougher and more inert materials.

In the year 1967, D. D. Zimskind and his collaborators developed a self-fastening catheter for extended drainage of urine, cystoscopically inserted. The main defect of this device was its easy migration or displacement.

R. P. Gibbons developed a silicone prosthesis, with multiple hairs or embossments, in order to guarantee its fastening, but which resulted in a prosthesis having a too large diameter.

D. L. MacCullough and T. N. Heperlen introduced the "J"-shaped flexible ends for prosthesis self-fastening.

In 1978, R. P. Finney produced the first prosthesis with both "J" ends similar to the present ones and it has to be reminded that it was in 1907 that Pousson developed the first "J" fastening.

As for the materials presently used, the material have a great influence on the physical properties and on the biocompatibility of the prosthesis. Thus the material choice is of particular importance.

Presently, the most commonly used materials are the silicone polymers, the polyurethanes, the silitec, the uro-soft and the c-flex. However, in continuous practice, these materials had serious problems associated with them. For example the silicone, which, because of being soft is very difficult to install; the uro-soft, which is very brittle; the polyurethane, which is stronger but has little, not to say nihil, radiopacity. In addition, the fact that the prosthesis is to be pierced makes that the holes are easily clogged and therefore their lack of comfort.

More recently an important conclusion was reached which was basic for practical applications of these prostheses: it was determined that calculus does not stick to the steel materials, but does stick to plastic and other organic materials.

C. Y. C. Pak, of the "Center for Mineral Metabolism" of the Southwestern Medical School of the University of Dallas, Tex., USA, reports this finding in his work entitled "Physicochemical Action and Extrarrenal Manifestations of Alkali Therapy, 1988". This conclusion is also reported in "Urologic research" of V. R. Walker, Rall Sutton and collaborators, of Plenum Press, New York, 1989.

This shows the importance of making the ureteral prosthesis according to the invention from steel, as is described hereinafter.

Finally, and with reference to the implantation methodology presently used, it must be stated that it is done by a retrograde route, preferably, through a cystoscope an urethroscope, an ureteral catheter or by an open route. It is also done by anterograde route, through a nephroscope, an urethroscope, open surgery or percutaneous nephrostonia.

Present technical modalities or methods used are: the simple endoscopic method, the radiologic endoscopic method, the method of reconversion of simple ureteral catheter or open surgery.

According to the invention, the lasting ureteral prosthesis comprises a tubular frame formed by a coiled metallic wire, which constitutes the wall of the prosthesis.

The spires of the wound metallic wire closely contact each preceding and following one, forming in this way a flexible hose but having permeable walls in both senses for liquids, in this case, the urine, for at least a portion of the length of the prosthesis. The length and gage of the hose so constituted is fixed and cannot be changed. In the event a different length or gage is required, a different model is to be applied.

Both ends of the helicoidal tubular prosthesis are approximately J-shaped in an undeformed curved shape and means for restoring the tubular prosthesis to its original undeformed configuration after a deformation are provided. In other words, the tubular prosthesis remembers or has a memory that allows it to immediately and always recover this special undeformed nonlinear shape at both ends.

This permits the introduction of the prosthesis through the urinary duct in a straight deformed configuration. The ends of the prosthesis recover their hook-like end shape at the moment both ends are in place in the patient, one of which is definitely located in the pelvis of the kidney and the other in the urinary bladder.

The interior of the prosthesis which is being described is provided with a very thin internal metallic wire, which practically does not diminish the span of the prosthesis, which is duly fastened, generally by welding, to both ends of the prosthesis and to the last few end spires of the helicoid wire at both ends. This prevents the elastic elongation of the prosthesis, which could otherwise occur due to opposed pulling forces on the prosthesis during a procedure.

In the procedure for locating the prosthesis, as a withdrawable fitting, a very long metallic rod whose length is greater than the prosthesis, for example approximately one and a half meters long, can be used. This rod is introduced in the interior of the prosthesis, which will then be deformed into the straight configuration facilitating its location. This rod in a preferred embodiment has a soft end, i.e., the one which is introduced in the interior of the patient's body, to avoid to injuring the interior of the organs through which it passes.

Once the prosthesis is located, the rod, as it was said, much longer than the prosthesis, can be easily withdrawn, an operation which is immediately carried out, pulling from the end which is exterior to the patient. The prosthesis being so located, and because of the essential characteristics already described as well as because of its material, as of its shape and construction, the prosthesis keeps the whole urinary duct open, the organic walls of which remain in contact with the external surface of the prosthesis, allowing, because of its elasticity, the passage of the urine toward the interior of the prosthesis, flowing along the hose section it forms, while the calculus will pass by the exterior of the prosthesis, preventing any clogging thereof.

Some drawings showing a preferred embodiment of the ureteral prosthesis are appended hereinbelow to this specification for nonlimiting exemplary purposes.

BRIEF DESCRIPTION OF THE DRAWING

The objects, features and advantages of the present invention will now be illustrated in more detail by the following detailed description, reference being made to the accompanying drawing in which:

FIG. 1 is a schematic, partly cross-sectional, partially side view of the ureteral prosthesis of the invention which shows the internal wire fastened in the prosthesis and the bending of both ends in the shape of hooks in a curved undeformed configuration;

FIG. 2 is a detailed perspective view of an end or mouth the ureteral prosthesis, showing the fastening of the internal wire by welding on the three or four final turns which prevents the elongation of the prosthesis;

FIG. 3 is a detailed side view of approximately J-shaped curved of the ureteral prosthesis;

FIG. 4 is a partially cutaway side view of the two ends of the ureteral prosthesis, where, in the interior thereof, the auxiliary rod has been inserted so that the prosthesis is deformed into a straight shape, which is best for introduction into the patient;

FIG. 5 is a schematic view which shows how the ureteral prosthesis is introduced into the patient with the assistance of the guiding rod, so the prosthesis finally can reach the pelvis, the urinary bladder and the ureter; and FIG. 6 is a similar schematic view similar to the preceding one, but showing the prosthesis already in position in the undeformed configuration having approximately J-shaped curved ends.

DESCRIPTION OF THE PREFERRED EMBODIMENT

According to the preferred embodiment shown in the drawings, the lasting ureteral prosthesis according to this invention, comprises the hollow tubular frame 1 consisting of the stainless and biotolerable metallic wire 2, wound in a coil comprising a plurality of contiguous contacting spires 4. The contiguous spires 4 contact each other, as can be seen in the FIGS. 1, 2, 3 and 4. However the shape of the coiled wire 2 permits the passage of the urine, outwardly from an inside region I to an outside region 0 and vice versa, as shown by the arrows A in FIG. 3, which occurs particularly at the openings between the spires in the vicinity of the approximately J-shaped ends 11,12.

In the interior of the tubular frame 1 an internal metallic wire 3 is arranged, the ends 11', 12' of which are welded to internal facing surfaces of the last three or four end spires 4 of the prosthesis, as is clearly shown in the FIG. 2.

When the ureteral prosthesis is to be placed in the interior of the urinary duct, a comparatively very long straight metallic rod 5 is inserted in the prosthesis as shown in FIG. 4, which deforms the hollow tubular frame 1 into a straight or linear shape and keeps the prosthesis straight. Just one end of this metallic rod 5, the very end which is to be introduced in the interior of the patient, is provided with a soft material end portion 6 which avoids attacking tissue through which it passes and therefore injury to the organism.

The prosthesis, as shown in FIG. 5, is inserted through the urinary bladder 7, and through the urinary duct 8, until at the pelvis 9 of the kidney and the kidney 10. The prosthesis thus located allows the normal flow of urine from the kidney 10 to the bladder 7, when a pathological process would occur if the prosthesis is not used. As is already mentioned, the urine is able to flow through the interior of the tubular frame 1, while calculus can pass between the frame 1 and the urinary duct 8.

The stability and removability of the prosthesis 1 is fully guaranteed by the winding of both hook-shaped ends 11 and 12 of it. Once they are located in the interior of the kidney 10 and of the bladder 7, respectively, as illustrated in FIG. 6, the ureteral prosthesis takes the underformed curved configuration or shape shown in the FIG. 1 with one of its approximately J-shaped ends in the pelvis 6 of the kidney. This curved shape is only changed when the guiding auxiliary internal rod 5 is inserted and then it is immediately recovered as soon as the rod is withdrawn.

The passage of the urine through the prosthesis of the invention is quite easy because of the fact that neither calculus nor deposits from the urine can stick to the material. The prosthesis produced with plastic material has holes, which are very easily clogged and which are impossible to clean. The urine passes outwardly from inside to outside or vice versa without hindrances and, more specifically, at its parts which take the shape of a hook, because more marked separations in the external surface are produced at the arches of the hook shaped parts.

After having described sufficiently the different essential features of this invention, it must be stated that sizes, internal features and variations which do not alter the essential shapes and quality of the materials and elements used, will not alter in any way the essential features of the invention, which are summarized in following claims.

While the invention has been illustrated and described as embodied in a lasting withdrawable ureteral prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Lasting withdrawable ureteral prosthesis comprising a hollow tubular frame having an outside region and an inside region, said hollow tubular frame consisting of a coiled biotolerable metallic wire formed into a plurality of contiguous contacting spires, and an internal metallic wire extending through the inside region of the hollow tubular frame from one end of the frame to another end thereof, said internal metallic wire being attached to at least three, but not more than four, of said spires at each of said ends to prevent elastic elongation of the coiled biotolerable metallic wire, wherein at least a portion of said spires permit a flow of urine between said spires from said inside region to said outside region and from said outside region to said inside region.

2. Lasting withdrawable ureteral prosthesis as defined in claim 1 wherein said internal metallic wire is attached to said spires at each of said ends of said hollow tubular frame by welding.

3. Lasting withdrawable ureteral prosthesis comprising a hollow tubular frame having an outside region and an inside region, said hollow tubular frame consisting of a coiled biotolerable metallic wire formed into a plurality of contiguous contacting spires, and an internal metallic wire extending through the inside region of the hollow tubular frame from one end of the hollow tubular frame to another end thereof, wherein said internal metallic wire is attached to at least three, but not more than four, of said spires at each of said ends of the hollow tubular frame to prevent elastic elongation of the coiled biotolerable metallic wire and said internal metallic wire has a curved undeformed configuration with approximately J-shaped internal wire ends in said curved undeformed configuration and, after being deformed from the curved undeformed configuration to a different configuration, said internal metallic wire returns to said undeformed configuration so that said tubular frame connected to said internal metallic wire assumes a curved shape with respective approximately J-shaped tubular frame ends when said approximately J-shaped internal wire ends are respectively arranged in a pelvis of a kidney and in a urinary bladder of a patient to prevent displacement from the pelvis of the kidney, wherein at least a portion of said spires of said hollow tubular frame permit a flow of urine between said spires from said inside region to said outside region and from said outside region to said inside region.

4. Lasting withdrawable ureteral prosthesis as defined in claim 3 and further comprising an auxiliary metallic rod having a length substantially greater than a length of the hollow tubular frame, having at least one soft and noninjurious end portion for keeping the hollow tubular frame in a straight shape during introduction into said patient and having means for withdrawal from the hollow tubular frame and the patient after the hollow tubular frame with the internal wire is in place in the patient.

5. Lasting withdrawable ureteral prosthesis as defined in claim 3, wherein said at least one portion of said spires allowing said flow of urine from said inside region to said outside region is located at at least one of said approximately J-shaped tubular frame ends of said hollow tubular frame.

\* \* \* \* \*

UNITED STATES PATENT AND TRADEMARK OFFICE
CERTIFICATE OF CORRECTION

PATENT NO. : 5,554,189
DATED : September 10, 1996
INVENTOR(S) : FERNANDO IZQUIERDO de la TORRE It is certified that error appears in the above-indentified patent and that said Letters Patent is hereby corrected as shown below:

On the title page: Item [76] should read -- Fernando Izquierdo de la Torre --.

Signed and Sealed this

Nineteenth Day of August, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,554,189
DATED : September 10, 1996
INVENTOR(S) : Fernando Izquierdo de la Torre It is certified that error appears in the above-identified patent and that said Letters Patent is hereby corrected as shown below:

On the title page, item [76], inventor, should read
-- Fernando Izquierdo de la Torre --.

Signed and Sealed this

Twenty-seventh Day of April, 1999

Attest:

Q. TODD DICKINSON

*Attesting Officer*    *Acting Commissioner of Patents and Trademarks*